United States Patent
Pearcey

(10) Patent No.: US 6,830,697 B1
(45) Date of Patent: Dec. 14, 2004

(54) FLUID TREATMENT SYSTEM, RADIATION SOURCE ASSEMBLY AND RADIATION SOURCE MODULE

(75) Inventor: Richard Pearcey, London (CA)

(73) Assignee: Trojan Technologies Inc., London (CA)

(*) Notice: Subject to any disclaimer, the term of this patent is extended or adjusted under 35 U.S.C. 154(b) by 140 days.

(21) Appl. No.: 10/070,165
(22) PCT Filed: Sep. 1, 2000
(86) PCT No.: PCT/CA00/01001
§ 371 (c)(1), (2), (4) Date: Mar. 4, 2002
(87) PCT Pub. No.: WO01/17906
PCT Pub. Date: Mar. 15, 2001

Related U.S. Application Data
(60) Provisional application No. 60/152,282, filed on Sep. 3, 1999.

(51) Int. Cl.$^7$ .................................................. C02F 1/32
(52) U.S. Cl. ....................... 210/748; 422/186.3; 250/435
(58) Field of Search .......................... 210/748, 745, 210/198.1, 205; 96/224; 422/24, 186.3; 250/432 R, 435, 436

(56) References Cited

U.S. PATENT DOCUMENTS

| | | | |
|---|---|---|---|
| 4,103,167 A | 7/1978 | Ellner | 250/432 |
| 4,204,956 A | 5/1980 | Flatow | 210/87 |
| 4,482,809 A | 11/1984 | Maarschalkerweerd | |
| 4,602,162 A | 7/1986 | Sperry, III et al. | 250/436 |
| 4,849,115 A * | 7/1989 | Cole et al. | 210/748 |
| 4,872,980 A | 10/1989 | Maarschalkerweerd | |
| 5,006,244 A | 4/1991 | Maarschalkerweerd | |
| 5,418,370 A * | 5/1995 | Maarschalkerweerd | 250/431 |
| 5,452,135 A | 9/1995 | Maki et al. | 359/834 |
| 5,539,210 A | 7/1996 | Maarschalkerweerd | |
| 5,590,390 A | 12/1996 | Maarschalkerweerd | |
| 5,660,719 A | 8/1997 | Kurtz et al. | 210/85 |
| 6,469,308 B1 * | 10/2002 | Reed | 250/436 |
| 6,518,577 B1 * | 2/2003 | Fang et al. | 250/372 |
| 6,646,269 B1 | 11/2003 | Traubenberg et al. | |

FOREIGN PATENT DOCUMENTS

| | | |
|---|---|---|
| DE | 297 07 052 U1 | 11/1997 |
| EP | 0 467 465 A1 | 1/1992 |
| JP | 2000-84545 A * | 3/2000 |

* cited by examiner

Primary Examiner—Frank M. Lawrence
(74) Attorney, Agent, or Firm—Katten Muchin Zavis Rosenman

(57) ABSTRACT

A radiation source module for use in a fluid treatment system. The radiation source module comprises: a frame (205) having a first support member, at least one radiation source assembly (125) extending from and in engagement with a first support member, the at least one radiation source assembly comprising at least one radiation source disposed within a protective sleeve; and an optical radiation sensor (150) disposed within the protective sleeve. The radiation source module is particularly useful in ultraviolet radiation treatment systems used to disinfect wastewater.

15 Claims, 3 Drawing Sheets

FLUID TREATMENT SYSTEM, RADIATION SOURCE ASSEMBLY AND RADIATION SOURCE MODULE

This application is a 371 of PCT/CA00/01001, and claims benefit of U.S. patent Application No. 60/152,282, filed Sep. 3, 1999.

TECHNICAL FIELD

In one of its aspects, the present invention relates to a radiation source assembly. In another of its aspects, the present invention relates to a radiation source module comprising a novel radiation source assembly having incorporated therein an optical radiation sensor.

BACKGROUND ART

Optical radiation sensors are known and find widespread use in a number of applications. One of the principal applications of optical radiation sensors is in the field of ultraviolet radiation fluid disinfection systems.

It is known that the irradiation of water with ultraviolet light will disinfect the water by inactivation of microorganisms in the water, provided the irradiance and exposure duration are above a minimum "dose" level (often measured in units of microWatt seconds per square centimeter). Ultraviolet water disinfection units such as those commercially available from Trojan Technologies Inc. under the tradenames UV700 and UV8000, employ this principle to disinfect water for human consumption. Generally, water to be disinfected passes through a pressurized stainless steel cylinder which is flooded with ultraviolet radiation. Large scale municipal waste water treatment equipment such as that commercially available from Trojan Technologies Inc. under the trade-names UV3000 and UV4000, employ the same principal to disinfect waste water. Generally, the practical applications of these treatment systems relates to submersion of treatment module or system in an open channel wherein the wastewater is exposed to radiation as it flows past the lamps. For further discussion of fluid disinfection systems employing ultraviolet radiation, see any one of the following:

U.S. Pat. No. 4,482,809,
U.S. Pat. No. 4,872,980,
U.S. Pat. No. 5,006,244,
U.S. Pat. No. 5,418,370,
U.S. Pat. No. 5,539,210, and
U.S. Pat. No. 5,590,390.

In many applications, it is desirable to monitor the level of ultraviolet radiation present within the water under treatment In this way, it is possible to assess, on a continuous or semi-continuous basis, the level of ultraviolet radiation, and thus the overall effectiveness and efficiency of the disinfection process.

It is known in the art to monitor the ultraviolet radiation level by deploying one or more passive sensor devices near the operating lamps in specific locations and orientations which are remote from the operating lamps. These passive sensor devices may be photodiodes, photoresistors or other devices that respond to the impingent of the particular radiation wavelength or range of radiation wavelengths of interest by producing a repeatable signal level (in volts or amperes) on output leads.

Conventional ultraviolet disinfection systems often incorporate arrays of lamps immersed in a fluid to be treated. Such an arrangement poses difficulties for mounting sensors to monitor lamp output. The surrounding structure is usually a pressurized vessel or other construction not well suited for insertion of instrumentation. Simply attaching an ultraviolet radiation sensor to the lamp module can impede flow of fluid and act as attachment point for fouling and/or blockage of the ultraviolet radiation use to treat the water. Additionally, for many practical applications, it is necessary to incorporate a special cleaning system for removal of fouling materials from the sensor to avoid conveyance of misleading information about lamp performance.

It would be desirable to have a radiation source assembly and module containing same which incorporated an optical radiation sensor that does not interfere with the flow of water or exposure of the fluid being treated to radiation.

DISCLOSURE OF THE INVENTION

It is an object of the present invention to provide a novel radiation source module which obviates or mitigates at least one of the above-mentioned disadvantages of the prior art.

It is another object of the present invention to provide a novel radiation source assembly which obviates or mitigates at least one of the above-mentioned disadvantages of the prior art.

Accordingly, in one of its aspects, the present invention provides a radiation source module for use of fluid treatment system, the module comprising:

a frame having a first support member;

at least one radiation source assembly extending from and in engagement (preferably sealing engagement) with a first support member, the at least one radiation source assembly comprising at least one radiation source disposed within a protective sleeve; and an optical radiation sensor disposed within the protective sleeve.

In another of its aspects, the present invention provides a radiation source assembly for use in a radiation source module, the radiation source assembly comprising at least one radiation source and an optical radiation sensor, both the at least one radiation source and the optical radiation sensor being disposed within a protective sleeve.

In yet another of its aspects, the present invention provides a fluid treatment system comprising:

a fluid treatment zone;

at least one radiation source assembly disposed in the fluid treatment zone, the at least one radiation source assembly comprising at least one radiation source disposed within a protective sleeve; and an optical radiation sensor disposed within the protective sleeve.

In a preferred embodiment of the fluid treatment system, the fluid treatment zone comprises a housing through which fluid flows. Preferably, the at least one radiation source assembly is secured to the housing.

Thus, the present inventor has discovered that, by placing an optical radiation sensor within a protective sleeve commonly employed in combination with a radiation source, a number of advantages accrue. For example, the need to periodically clean the surface of the sensor from fouling materials is obviated since the sensor is disposed within the protective sleeve. This is particularly advantageous when the radiation source assembly is used in conjunction with a cleaning system (e.g., one of the cleaning systems in the '370, '210 and/or '390 patents referred to above). Specifically, since the cleaning system serves the purpose of removing fouling materials from the protective sleeve to allow for optimum dosing of radiation, a separate cleaning system for the sensor is not required. Further, since the optical radiation sensor is disposed within an existing element (the protective sleeve) of the radiation source module, incorporation of the sensor in the module does not result in any additional hydraulic head loss and/or does not create a "catch" for fouling materials. Other advantages will be apparent to those skilled in the art.

BRIEF DESCRIPTION OF THE DRAWINGS

Embodiments of the present invention will be described with reference to the accompanying drawings, in which.

BEST MODE FOR CARRYING OUT THE INVENTION

Figure 1:
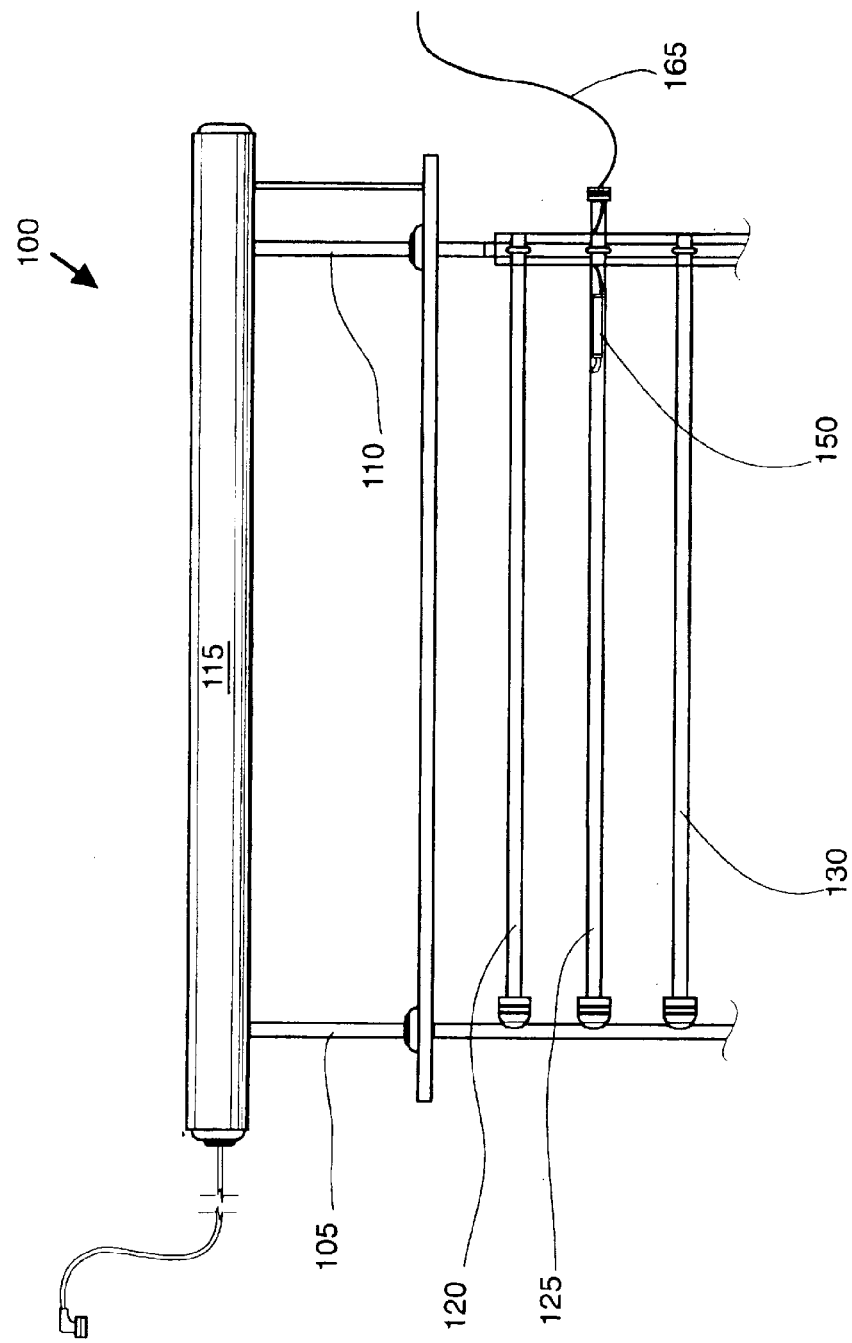
FIG. 1 is a side elevation of an embodiment of the present radiation source module.
Figure 2:
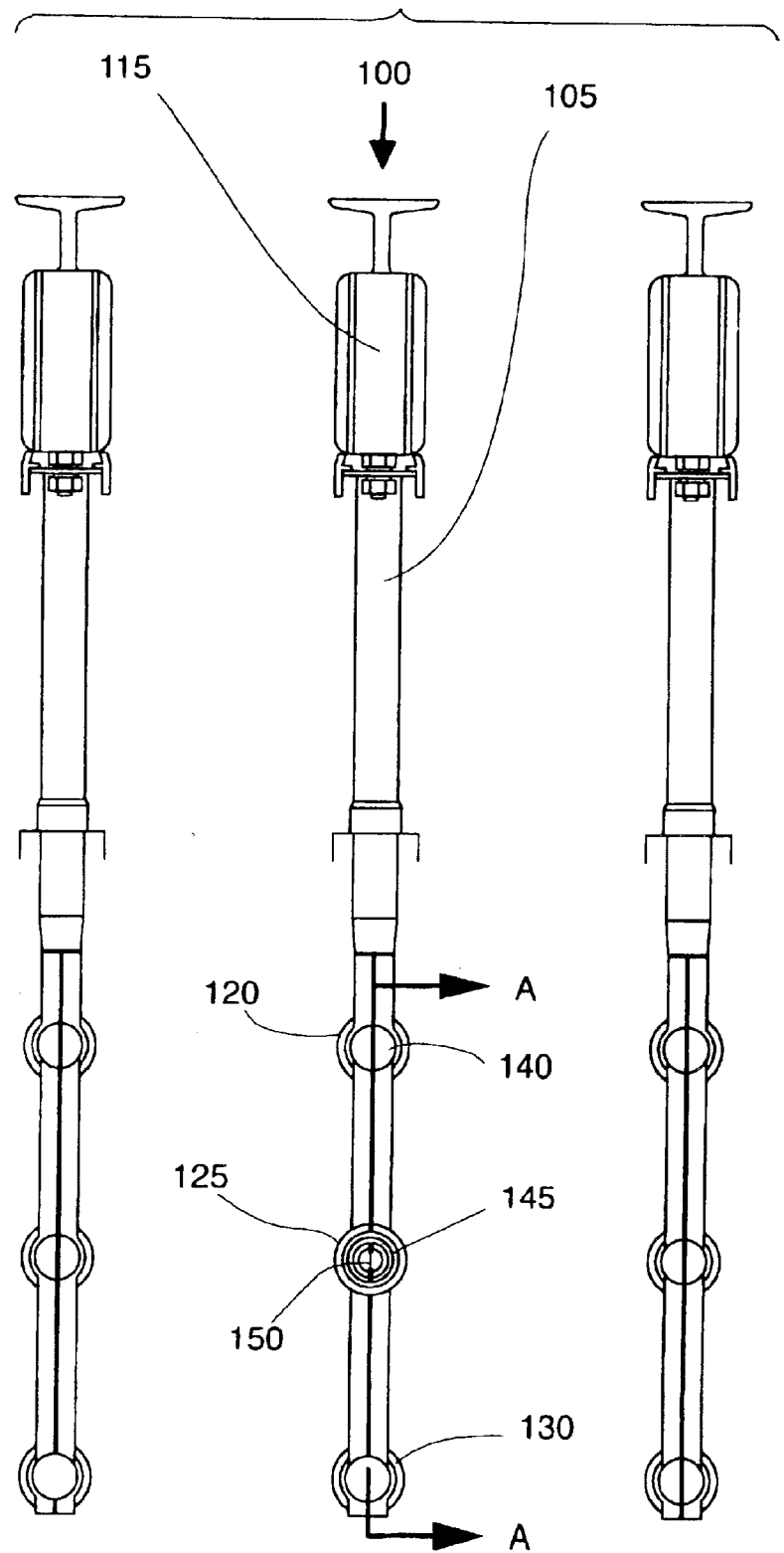
FIG. 2 is a sectional view of a trio of radiation source modules including the radiation source module illustrated in FIG. 1.

With reference to FIGS. 1–2, a radiation source module 100 is illustrated. Radiation source module 100 comprises a pair of support legs 105,110 depending from a crosspiece 115. Disposed between support legs 105,110 are a trio of radiation source assemblies 120,125,130. Each radiation source assembly 120,125,130 comprises a radiation source 140 (e.g., an ultraviolet emitting lamp) disposed within a protective sleeve 145 (e.g., typically made of quartz). The design of support legs 105,110 and radiation source assemblies 120 is preferably as is described in U.S. Pat. Nos. 4,872,980 and 5,006,244 referred to hereinabove.

Preferably, each protective sleeve 145 is connected to support leg 105 via a coupling nut 140. The details of this connection are preferably as set out in copending U.S. patent application Ser. No. 09/258,142 (Traubenberg et al.), now U.S. Pat. No. 6,646,269.

Figure 3:
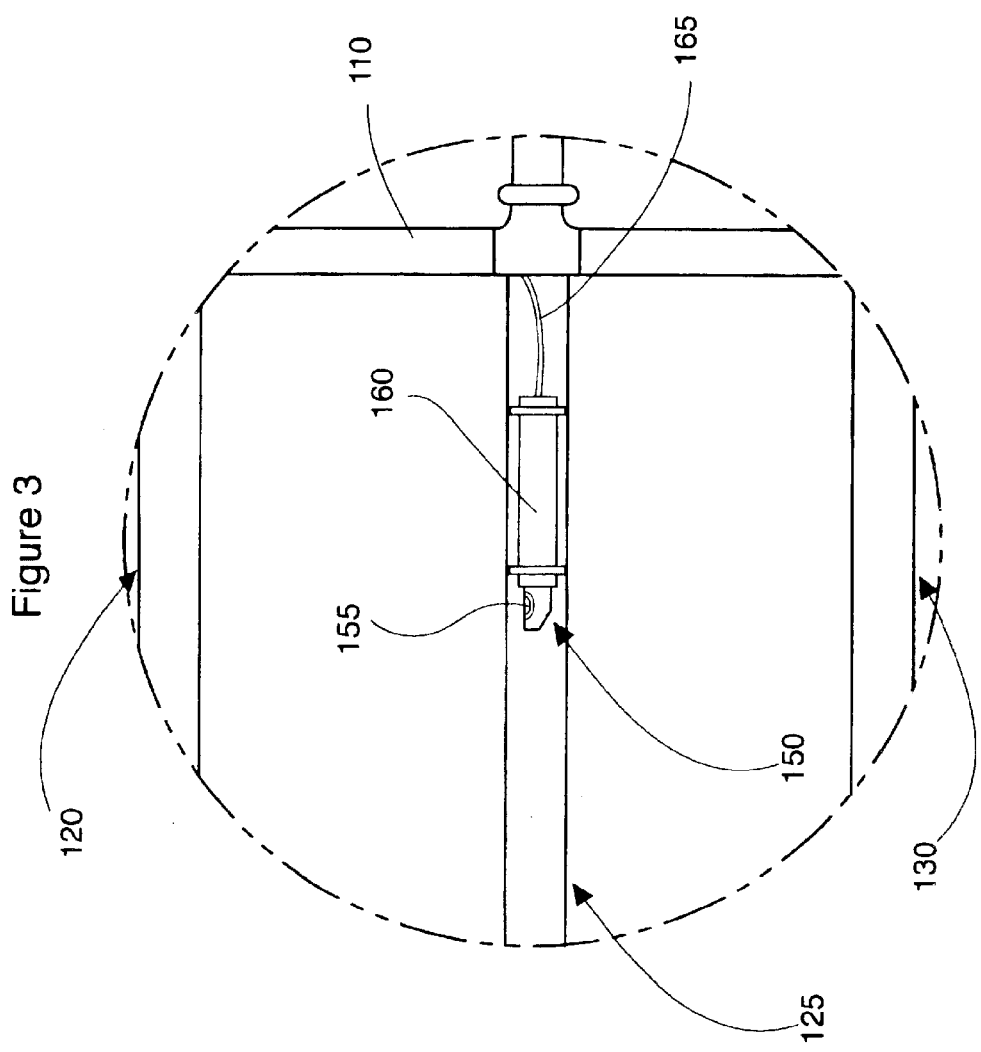
FIG. 3 illustrates an enlarged sectional view taken along line A—A in FIG. 2.

With reference to FIGS. 2 and 3, radiation source assembly 125 comprises an optical radiation sensor 150 disposed within protective sleeve 145 adjacent support leg 110. Optical sensor 150 comprises a window 155(optional) which receives incident radiation and passes this radiation into a body 160 that contains a photodiode (not shown) or other radiation sensor material as described above. A signal related to the amount of radiation sensed is then sent from body 160 through a lead 165 which is connected to a conventional control system which allows the user to ascertain the level of radiation sensed compared to a predetermined benchmark.

Preferably, sensor 160 is oriented within protective sleeve 145 in a manner that it receives incident radiation from at least one, preferably both, of adjacent radiation source assemblies 120,130. In other words, it is preferred that sensor 150 not receive incident radiation from the radiation source contained within the same protective sleeve in which sensor 150 is housed.

The sensor itself maybe chosen from conventional sensors. For example, a suitable sensor is commercially available from UDT Sensors Inc. (Hawthorne, Calif.).

As shown in FIG. 2, radiation source module 100 may be a member of an array of radiation source modules which do not contain an optical radiation source sensor. Thus, the trio of radiation source modules illustrated in FIG. 2 could be placed in an open channel as shown in U.S. Pat. Nos. 4,872,980 and 5,006,244 and used to treat wastewater as set out in those patents.

While the present invention has been described with reference to preferred and specifically illustrated embodiments, it will of course be understood by those skilled in the arts that various modifications to these preferred and illustrated embodiments may be made without the parting from the spirit and scope of the invention. For example, while the present invention has been illustrated with reference to radiation source modules similar in general design to those taught in U.S. Pat. Nos. 4,872,980 and 5,006,244, it is possible to employ the present radiation source assembly in a module such as the one illustrated in U.S. Pat. Nos. 5,418,370, 5,539,210 and 5,590,390—i.e., in a module having a single support for one or more elongate source assemblies extending therefrom. Further, it is possible to employ the present radiation source. assembly in a fluid treatment device such as those commercially available from Trojan Technologies Inc. under the tradenames UV700 and UV8000. Still, further, while, in the embodiments illustrated and described above, the optical sensor is disposed at the end of the projective sleeve opposite the end where electrical connections for the lamp are located, it possible to locate the optical radiation sensor at the same end as the electrical connections for the lamp thereby allowing for use of the protective sleeve having one closed end. Still further, it is possible to utilize an optical radiation source sensor disposed between two radiation sources, all of which are disposed within a protective sleeve. Other modifications which do not depart from the spirit and scope of the present invention will be apparent to those skilled in the art.

All publications, patents and patent applications referred to herein are incorporated by reference in their entirety to the same extent as if each individual publication, patent or patent application was specifically and individually indicated to be incorporated by reference in its entirety.

What is claimed is:

1. A fluid treatment system radiation source module, comprising:
   a frame having a first support member;
   a plurality of radiation source assemblies extending from and in engagement with said first support member, each radiation source assembly comprising at least one radiation source disposed within a protective sleeve; and
   an optical radiation sensor disposed within the protective sleeve of at least one of the plurality of radiation source assemblies, at least one radiation source assembly having no optical radiation sensor.

2. The radiation source module defined in claim 1, wherein the frame further comprises a second support member opposed to and laterally spaced from the first support member, the plurality of radiation source assemblies being disposed between each of the first support member and the second support member.

3. The radiation source module defined in claim 2, wherein the frame further comprises a third support member interconnecting the first support member and the second support member.

4. The radiation source module defined in claim 1, wherein the frame further comprises a ballast for controlling the radiation sources.

5. The radiation source module defined in claim 1, wherein the first support member comprises a hollow passageway for receiving at last one lead wire for conveying electricity to the radiation sources.

6. The radiation source module defined in claim 1, wherein each protective sleeve comprises a quartz sleeve.

7. The radiation source module defined in claim 1, wherein each radiation source assembly comprises a plurality of radiation sources.

8. The radiation source module defined in claim 1, wherein the optical radiation sensor is disposed adjacent one end of the protective sleeve.

9. A water treatment radiation source assembly, comprising:

a plurality of radiation source modules, each having a protective sleeve; and an optical radiation sensor disposed within the protective sleeve of at least one of the radiation source modules, at least one of the radiation source module protective sleeves having no radiation sensor.

10. The radiation source assembly defined in claim 9, wherein each the protective sleeve comprises a quartz sleeve.

11. The radiation source assembly defined in claim 9, wherein each radiation source module comprises a plurality of radiation sources.

12. The radiation source assembly defined in claim 9, wherein the optical radiation sensor is disposed adjacent one end of the protective sleeve.

13. A fluid treatment system comprising:

a fluid treatment zone;

a plurality of radiation source assemblies disposed in the fluid treatment zone, at least one radiation source assembly comprising at least one radiation source disposed within a protective sleeve; and an optical radiation sensor disposed within the protective sleeve, at least one radiation source assembly having no optical radiation sensor.

14. The fluid treatment system defined in claim 13, wherein the fluid treatment zone comprises a housing through which fluid flows.

15. The fluid treatment system defined in claim 14, wherein each radiation source assembly is secured to the housing.

\* \* \* \* \*